United States Patent [19]

Abdallah

[11] 4,020,167

[45] Apr. 26, 1977

[54] ETHANOL INTOXICATION WITH 2[(3-TRIFLUOROMETHYLPHENOXY)METHYL]-2-IMIDAZOLINE

[75] Inventor: Abdulmunien H. Abdallah, Midland, Mich.

[73] Assignee: The Dow Chemical Company, Midland, Mich.

[22] Filed: Oct. 16, 1975

[21] Appl. No.: 623,178

[52] U.S. Cl. .............................................. 424/273
[51] Int. Cl.² ..................................... A61K 31/415
[58] Field of Search ................ 424/273; 260/309.6

[56] References Cited

UNITED STATES PATENTS

| | | | |
|---|---|---|---|
| 3,449,354 | 6/1969 | White | 260/465 F |
| 3,449,355 | 6/1969 | White | 260/309.6 |
| 3,449,356 | 6/1969 | White | 260/309.6 |
| 3,449,357 | 6/1969 | White | 260/465 F |
| 3,449,501 | 6/1969 | Rudzik | 424/273 |
| 3,860,719 | 1/1975 | Marshall | 424/273 |

*Primary Examiner*—Norman A. Drezin
*Attorney, Agent, or Firm*—James W. Ambrosius

[57] ABSTRACT

A novel method for combatting ethanol intoxication and narcosis in animals by administering an effective amount of the compound 2[(3-trifluoromethylphenoxy)methyl]-2-imidazoline or a pharmaceutically-acceptable salt thereof internally to the animal is disclosed.

5 Claims, No Drawings

ETHANOL INTOXICATION WITH 2[(3-TRIFLUOROMETHYLPHENOXY)METHYL]-2-IMIDAZOLINE

SUMMARY OF THE INVENTION

This invention is concerned with a method for combatting ethanol intoxication and narcosis in mammals which comprises administering an imidazoline compound to a mammal in an amount sufficient to antagonize ethanol intoxication and narcosis. The activity is exhibited by 2[(3-trifluoromethylphenoxy)methyl]-2-imidazoline and its pharmaceutically-acceptable salts.

It has been found that 2((3-trifluoromethylphenoxy)methyl]-2-imidazoline and the pharmaceutically-acceptable salts thereof have the useful property of antagonizing the central nervous system depressant effects of ethanol when administered to animals, and in particular, to mammals intoxicated or narcotized with ethanol. This activity is coupled with a relatively low mammalian toxicity. As employed herein, the phrase "pharmaceutically acceptable salts" refers to non-toxic acid addition salts of the imidazoline compound, the anions of which are relatively innocuous to animals at dosages consistent with good ethanol antagonizing activity so that beneficial effects of the free base are not vitiated by side effects ascribable to the anions. Pharmaceutically-acceptable salts include those derived from mineral acids such a hydrochloric, hydrobromic, sulfuric, and nitric acids and from organic acids such as acetic, lactic, maleic, succinic, fumaric, glutaric, citric, malic, p-toluenesulfonic, and tartaric acids, and the like.

Prior Art

It is known in the art that many imidazoline compounds are biologically active. Certain imidazolines having analgesic and anti-inflammatory activity have been reported. Rudzik, U.S. Pat. No. 3,449,501; White U.S. Pat. No. 3,449,356. Specifically, 2-[(2-trifluoromethylphenoxy) methyl]-2-imidazoline is a known antidepressant. White, U.S. Pat. No. 3,449,354. Additionally, the imidazoline compound, 2](3,4-dichlorophenoxy)methyl]-2-imidazoline is reported to have an antagonistic effect on ethanol intoxication. Marshall, U.S. Pat. No. 3,860,719. This latter activity is not a common or predictably property of imidazolines and, except for the activity reported for 2-[(3,4-dichlorophenoxy)methyl]-2-imidazoline does not appear to be present in the known imidazolines. Therefore it is unexpected and not predictable that the compound herein described having substitutions on the benzene ring which differ markedly from the prior reported antagonist also should have such activity.

DETAILED DESCRIPTION OF THE INVENTION

The 2[(3-trifluoromethylphenoxy)methyl]-2-imidazoline compound can be prepared by the reaction of the corresponding $\alpha,\alpha,\alpha$-trifluoro-m-toloxy acetic acid or $\alpha,\alpha,\alpha$-trifluoro-m-toloxy acetonitrile eith ethylenediamine monotosylate by the procedure disclosed by White, U.S. Pat. NO. 3,449,355. The pharmaceutically-acceptable salts are prepared by dissolving the free base compound in an alcohol and adding an excess of an alcoholic solution of an appropriate acid such as, for example hydrochloric acid, acetic acid, maleic acid or the like to precipitate the pharmaceutically-acceptable salt. The salt can be separated by filtration and purified by recrystallization; alternatively other recovery and purification procedures can be employed as known to one skilled in the art.

In accordance with the method of the present invention, an ethanol-antagonizing amount of 2[(3-trifluoromethylphenoxy)methyl]-2-imidazoline or a pharmaceutically-acceptable salt thereof is administered internally to a mammal. More specifically the imidazoline compound is administered internally to an animal, usually by injection or by oral administration, in a manner so as to introduce an ethanol-antagonizing amount of said compound into the blood stream. Ethanol antagonism can be achieved when the compound is administered prior to administration or consumption of ethanol, provided the ethanol is introduced into the animals' system at a time when the blood level of the imidazoline compound is sufficient to produce the alcohol-antagonizing effect.

The amount of the imidazoline compound to be administered to a mammal in particular cases will vary depending upon such factors as the ethanol blood level, degree of intoxication or narcosis to be alleviated, the presence of ethanol in the gastrointestinal tract, the route of administration, the exact effect to be produced, whether or not the free base or a pharmaceutically-acceptable salt or the mixed benzenamine compound is employed, whether or not the compound is employed prophylactically or therapeutically, e.g., as an antidote, and the species, size, weight, age, and physical condition of the particular animal being treated. Usually the compound will be administered so as to provide an active ingredient ranging from about 1 or less to about 35mg/kg animal body weight when given by intravenous injection or from about 1 or less to about 70 mg/kg by parenteral routes other than intravenous.

The benzenamine compound can be formulated with conventional pharmaceutical carriers in known procedures. The selection of the exact pharmaceutical carrier to be employed in any given circumstance can be carried out by standard and conventionally employed range finding operations to produce the compositions and formulations of the present invention having the desired characteristics of physical form, ease of administration by a desired route, storage stability, etc.

A distinct advantage offered by the salt employed in the practice of the present invention over the known 2-[(3,4-dichlorophenoxy)methyl]-2-imidazoline salt is the relatively low mammalian toxicity of the disclosed ethanol antagonist compound. The toxicity data presented in Table I shows that the median lethal dose ($LD_{50}$) in mice of the disclosed compound is twice the median lethal dose ($LD_{50}$) of 2-[(3,4-dichlorophenoxy)methyl]-2-imidazoline hydrochloride.

TABLE I

| Compound | $LD_{50}$ | Route |
|---|---|---|
| 2-[(3,4-dichlorophenoxy)methyl]-2-imidazoline hydrochloride | 41 mg/kg | IP* |
| 2[(3-trifluoromethylphenoxy)-methyl]-2-imidazoline hydrochloride | 83 mg/kg | IP* |

*Given by intraperitoneal injection

DESCRIPTION OF THE PREFERRED EMBODIMENT

As a control study seven groups of mice (controls) containing 10 mice each were administered 4.4 ml/kg of ethanol by intraperitoneal injection. Administration of this dosage of ethanol was observed to induce complete narcosis in most individuals. The animals were observed to lose their righting reflex within ten minutes after administration of the ethanol. The unconscious mice were placed on their backs, and the duration of narcosis (mean sleep time) was measured by observing the time the animal remained unconscious following administration of the ethanol until the time the animal spontaneously righted itself.

A group of ten mice (protected mice) was administered 10 mg/kg of 2[(3-trifluoromethylphenoxy)methyl]-2-imidazoline hydrochloride by intravenous injection. Five minutes later the mice were given an intraperitoneal injection of 4.4 ml/kg of ethanol. After narcosis developed the mice were placed on their backs, and the time when they regained their righting reflex was recorded. The results of the study are summarized in Table II.

TABLE II

|  | Mean Sleep Time ±S.E.* | Number of Mice with 0 sleep time |
|---|---|---|
| Protected Mice | 9.70 ± 6.85 min. | 6 |
| Controls | 61.60 ± 11.85 min. | 1 |

*S.E. = Standard Error of the Mean

It should be noticed that in the protected mice six of the animals never became unconscious while in the control animals one animal remained conscious after ethanol injection. Further, for the mice which did become unconscious the time of recovery was almost seven times faster for the protected animals.

In a similar manner to the above, quantities of 2[(3-trifluoromethylphenoxy)methyl]-2-imidazoline ranging from about 1 to 70 mg/kg of animal body weight can be injected into or ingested orally by animals to combat ethanol intoxication and narcosis. Similar results would be obtained with the other pharmaceutically-acceptable salts.

I claim:
1. A method for combatting ethanol intoxication and narcosis in mammals comprising administering internally to an intoxicated mammal an ethanol intoxication and narcosis antagonizing amount of 2((3-trifluoromethylphenoxy)methyl)-2-imidazoline or a pharmaceutically-acceptable salt thereof.

2. A method of protecting a mammal from ethanol intoxication or narcosis which comprises administering internally to the mammal an ethanol intoxication and narcosis antagonizing amount of 2-((3-trifluoromethylphenoxy)methyl)-2-imidazoline or a pharmaceutically-acceptable salt thereof prior to administration of a narcotizing amount of ethanol with the proviso that the ethanol is administered at a time when the blood level of the imidazoline compound is sufficient to produce an ethanol-antagonizing effect.

3. The method of claim 1 wherein the dose administered orally or by injection is from 1 to 70 milligrams of the imidazoline compound per kilogram of body weight.

4. The method of claim 1 wherein the intravenous dose is from 1 to 35 milligrams of the imidazoline compound per kilogram of body weight.

5. The method of claim 1 wherein the compound is 2[(3-trifluoromethylphenoxy)methyl]-2-imidazoline hydrochloride.

* * * * *